US00PP22520P2

(12) United States Plant Patent
Smith

(10) Patent No.: US PP22,520 P2
(45) Date of Patent: Feb. 21, 2012

(54) ***SALVIA* PLANT NAMED 'ORCHID GLOW'**

(50) Latin Name: *Salvia hybrida*
Varietal Denomination: Orchid Glow

(75) Inventor: M. Nevin Smith, Watsonville, CA (US)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 12/805,732

(22) Filed: Aug. 17, 2010

(51) Int. Cl.
*A01H 5/00* (2006.01)

(52) U.S. Cl. ..... Plt./475
(58) Field of Classification Search ..... Plt./475
See application file for complete search history.

*Primary Examiner* — June Hwu
(74) *Attorney, Agent, or Firm* — Buchanan Ingersoll & Rooney PC

(57) ABSTRACT

A new and distinct *Salvia* plant of unknown parentage is provided that was discovered in a nursery setting while growing among other *Salvia* plants. Over a long blooming season attractive blossoms are formed that are magenta-purple in coloration. The growth habit is upright and bushy. The foliage is large and bright green in coloration. Following pruning, the plant displays a tendency to vigorously regrow. The plant is well suited for providing attractive ornamentation.

1 Drawing Sheet

Botanical/commercial classification: *Salvia hybrida/ Salvia* Plant.

Varietal denomination: cv. Orchid Glow.

SUMMARY OF THE INVENTION

The new *Salvia* cultivar of the present invention was discovered during August or September, 2005, while growing in a plant nursery setting among other *Salvia* plants at Watsonville, Calif., U.S.A. The new cultivar is of unknown parentage and likely includes *Salvia microphylla* in its ancestry. The new plant was distinguished from other *Salvia* plants growing in the nursery where it was discovered primarily through a study of its distinctive blossom coloration combined with other attractive botanical characteristics identified hereafter. Had the single plant of the present invention not been discovered and carefully preserved, it would have been lost to mankind.

The plant is a perennial that can be grown to advantage without protection in U.S.D.A. Hardiness Zone Nos. 7 to 11.

It was found that the new *Salvia* cultivar possesses the following combination of characteristics:

(a) displays an upright and bushy growth habit,
(b) forms in abundance over a long blooming season attractive blossoms that are magenta-purple in coloration,
(c) displays vigorous large bright green foliage,
(d) displays a tendency to vigorously regrow following pruning, and
(e) is well suited for providing attractive ornamentation.

The new cultivar of the present invention can be readily distinguished from other *Salvia* cultivars, such as the *Salvia greggii* 'Ultra Violet' cultivar (non-patented in the United States), upon an inspection of the blossoms. The 'Ultra Violet' cultivar forms smaller blossoms that are true purple in coloration. Unlike the new cultivar, the blossoms of the 'Ultra Violet' cultivar are Purple-Violet Group 81A in coloration by reference to the R.H.S. Colour Chart of the Royal Horticultural Society, London, England.

The new cultivar well meets the needs of the horticultural industry and can be grown to advantage as attractive ornamentation in parks, gardens, public areas, and residential landscapes. The magenta-purple blossoms contrast nicely with the large bright green foliage.

The new cultivar has been asexually reproduced by the rooting of cuttings for several generations. Such asexual reproduction as performed at Watsonville, Calif., U.S.A., and near West Grove, Pa., U.S.A., has demonstrated that the characteristics of the new cultivar are firmly fixed and stable and are strictly transmissible from one generation to another. Accordingly, the new cultivar asexually reproduces in a true-to-type manner from one generation to another.

The new cultivar has been named 'Orchid Glow'.

Brief Description of the Photograph

The accompanying photograph shows as nearly true as it is reasonably possible to make the same, in a color illustration of this character, a close view of a typical specimen of the new cultivar while growing outdoors. The magenta-purple blossoms are illustrated as is the large bright green foliage. The plant had been reproduced by the rooting of a cutting in a greenhouse and subsequently had been grown outdoors near West Grove, Pa., U.S.A. The photograph was obtained during July 2010 when the plant was approximately one year of age.

DETAILED DESCRIPTION

The chart used in the identification of colors is that of the Royal Horticultural Society (R.H.S. Colour Chart—1995) of London, England. Color terminology in common terms sometimes is included as an aid to the reader. Such color terminology is to be accorded its customary dictionary significance. The description is based on the observation of typical specimens of the new cultivar at an age of approximately one year during July 2010 while growing in containers outdoors near West Grove, Pa., U.S.A.

Plant:

*Form*.—Bushy, vigorous, and generally upright.

*Height*.—Commonly up to approximately 47 cm on average.

*Width*.—Commonly approximately 50 cm on average.
*Growth habit*.—Perennial in U.S.D.A. Hardiness Zone Nos. 7 to 11.
*Leaf arrangement*.—Opposite.
*Leaf configuration*.—Elliptic to ovate.
*Leaf length*.—Commonly approximately 2 to 3.5 cm on average.
*Leaf width*.—Commonly approximately 0.5 to 2 cm on average.
*Leaf margin*.—Crenate.
*Leaf texture*.—Commonly slightly fleshy.
*Leaf blade color*.—Green Group 137C on the upper surface, and Yellow-Green Group 147A on the under surface.
*Leaf blade apex*.—Acute to obtusely rounded and sometimes cuspidate.
*Leaf blade base*.—Mainly obtuse.
*Scent*.—Leaves commonly display a tangy fruity scent when crushed.
*Petiole shape*.—Somewhat flattened.
*Petiole length*.—Variable and commonly approximately 1 to 1.6 cm.
*Petiole width*.—Commonly approximately 1 to 1.5 mm.
*Petiole texture*.—Smooth.
*Petiole color*.—Yellow-Green Group 144B.

Inflorescence:
*Time*.—prolonged blooming period beginning in May and extending into September.
*Bud shape*.—Oblanceolate.
*Bud size*.—Approximately 1 cm.
*Bud color*.—Yellow-Green Group 145A overlaid with Greyed-Purple Group 187A.
*Type*.—Terminal raceme.
*Diameter*.—Commonly approximately 2 cm for an individual flower on average and approximately 7 cm for a terminal raceme at the widest point including the width of the lower lip on average.
*Length*.—Commonly approximately 3 cm for an individual flower on average, and approximately 17 cm for a terminal raceme on average.
*Number*.—Commonly up to approximately 40 flowers per plant on average.
*Configuration*.—Tubular, and two-lipped.
*Pedicel length*.—Commonly approximately 3 to 4 mm on average.
*Pedicel width*.—Commonly approximately 2 mm on average.
*Pedicel texture*.—Glabrous.
*Pedicel color*.—Green, Yellow-Green Group 145B, and somewhat infused with Greyed-Purple Group 187A.
*Calyx shape*.—Broadly campanulate, and flared towards the apex.
*Calyx rib number*.—Commonly 12, and longitudinally disposed.
*Calyx length*.—Commonly approximately 15 mm on average.
*Calyx width*.—Commonly up to 5 mm.
*Calyx texture*.—Glandular and puberulent on the upper and under surfaces.
*Calyx color*.—On the upper lobe Violet Group 83D at the apex and Yellow-Green Group 145B at the base, and on the lower lobes primarily Yellow-Green Group 145B.
*Calyx lobe number*.—3.
*Calyx upper lobe number*.—1.
*Calyx upper lobe shape*.—Acute.
*Calyx upper lobe length*.—Commonly approximately 4 mm on average.
*Calyx upper lobe width*.—Commonly approximately 4 mm in width.
*Calyx lower lobe number*.—2.
*Calyx lower lobe shape*.—Acute.
*Calyx lower lobe length*.—Commonly approximately 3 mm on average.
*Calyx lower lobe width*.—Commonly approximately 4 mm on average.
*Corolla shape*.—Tubular proximally to two-lipped distally.
*Corolla length*.—Commonly approximately 2.2 to 2.5 cm on average.
*Corolla diameter*.—Approximately 0.4 cm.
*Corolla color*.—The base commonly is near Yellow-White Group 158D, the tube is near Red-Purple Group 74A, the upper lip is near Red-Purple Group 72A, the lower lip is near Red-Purple Group 74A, and the inner corolla tube is a blend of Red-Purple Group 72A and White Group 155B.
*Corolla tube length*.—Approximately 23 mm on average.
*Corolla tube width*.—Approximately 3 mm on average.
*Corolla tube depth*.—Approximately 10 mm on average.
*Corolla tube lip number*.—2.
*Corolla upper lip number*.—1.
*Corolla upper lip shape*.—Hood-like.
*Corolla upper lip length*.—Commonly approximately 9 mm average.
*Corolla lower lip length*.—2, suborbicular.
*Corolla lower lip shape*.—Banner-like, and extended downward.
*Corolla lower lip outline*.—Obovate.
*Corolla lower lip length*.—Commonly approximately 12 mm on average.
*Corolla lower lip diameter at tip*.—Approximately 12 mm on average.
*Pistil number*.—1.
*Style length*.—Approximately 2.5 cm on average.
*Style width*.—Commonly approximately 1 mm on average.
*Style attachment site*.—At four-lobed ovary between lobes.
*Stamen number*.—2.
*Stamen shape*.—Seesaw-like.
*Filament length*.—Approximately 6 mm on average.
*Connective length*.—Approximately 12 mm on average.
*Anther length*.—Approximately 2 mm on average.
*Anther width*.—Approximately 1 mm on average.
*Anther color*.—Yellow-Orange Group 16A.
*Anther attachment site*.—At outer end of the connective.
*Fruit*.—None observed during observations to date.

Development:
*Vegetation*.—Vigorous and displays a tendency to quickly regrow following pruning.
*Blooming*.—Displays long blooming season.
*Fertility*.—Not observed with the plants being sterile during observations to date.
*Winter hardiness*.—The plant is a perennial that can be grown in at least U.S.D.A. Hardiness Zone Nos. 7 to 11.

*Disease resistance*.—No particular sensitivity to disease has been encountered during observations to date.

I claim:

1. A new and distinct *Salvia* plant characterized by the following combination of characteristics:

(a) displays an upright and bushy growth habit, (b) forms in abundance over a long blooming season attractive blossoms that are magenta-purple in coloration, (c) displays vigorous large bright green foliage, (d) displays a tendency to vigorously regrow following pruning, and (e) is well suited for providing attractive ornamentation; substantially as illustrated and described.

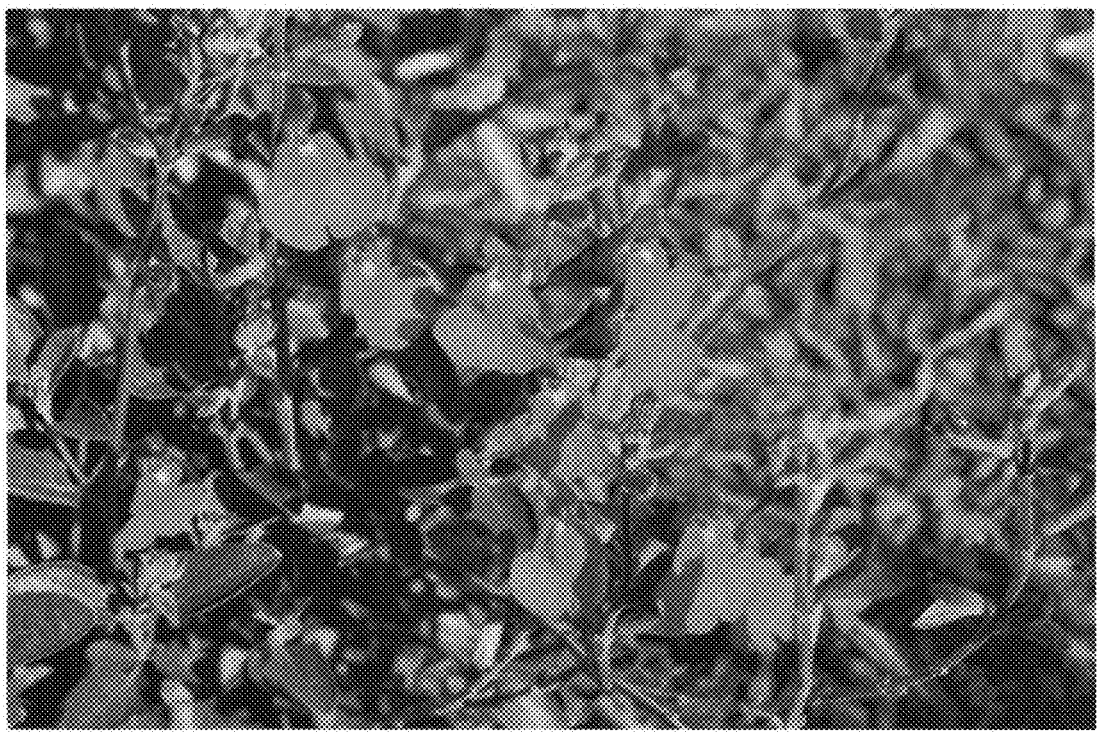

* * * * *